United States Patent
Bernstein et al.

(10) Patent No.: US 7,776,039 B2
(45) Date of Patent: Aug. 17, 2010

(54) ANTERIOR CRUCIATE LIGAMENT TETHER

(76) Inventors: Joseph Bernstein, 761 Millbrook La., Haverford, PA (US) 19041; James L. Carey, 4007 Auburn La., Nashville, TN (US) 37215

(*) Notice: Subject to any disclaimer, the term of this patent is extended or adjusted under 35 U.S.C. 154(b) by 746 days.

(21) Appl. No.: 11/526,545

(22) Filed: Sep. 25, 2006

(65) Prior Publication Data

US 2008/0097430 A1   Apr. 24, 2008

(51) Int. Cl.
A61F 2/08 (2006.01)
(52) U.S. Cl. .................. 606/74; 623/13.11; 623/13.12; 623/13.13; 623/13.14; 623/13.18
(58) Field of Classification Search .......... 606/65, 606/88, 89, 98, 138, 154, 228, 232, 233; 623/13.11–13.14, 13.18

See application file for complete search history.

(56) References Cited

U.S. PATENT DOCUMENTS

| | | | |
|---|---|---|---|
| 4,696,293 A | 9/1987 | Ciullo | |
| 4,697,583 A | 10/1987 | Mason | |
| 4,739,751 A | 4/1988 | Sapega | |
| 5,139,520 A * | 8/1992 | Rosenberg | 606/87 |
| 2002/0133108 A1* | 9/2002 | Jagodzinski | 602/16 |
| 2005/0192581 A1* | 9/2005 | Molz et al. | 606/74 |
| 2007/0233241 A1* | 10/2007 | Graf et al. | 623/13.14 |
| 2007/0270804 A1* | 11/2007 | Chudik | 606/60 |
| 2008/0004702 A1* | 1/2008 | Denoziere | 623/17.13 |

OTHER PUBLICATIONS

Kurosaka M, et al. Spontaneous healing of a tear of the anterior cruciate ligament. J Bone Joint Surg. 80-A: 1200-1203. 1998.
Irvine GB, Glasgow MMS. The natural history of the meniscus in anterior cruciate deficiency. J Bone Joint Surg. 74-B: 403-405. 1992.
Indelicato PA. Non-operative treatment of complete tears of the medial collateral ligament of the knee. J Bone Joint Surg. 65-A: 323-329. 1983.
Kocher MS, et al. Determinants of patient satisfaction with outcome after anterior cruciate ligament reconstruction. J Bone Joint Surg. 84-A: 1560-1572. 2002.
Marshall JL, et al. The anterior cruciate ligament: a technique of repair and reconstruction. Clin Orthop. 143: 97-106. 1979.
Gollehon DL, Warren RF, Wickiewicz TL. Acute repairs of the anterior cruciate ligament—past and present. Orthop Clin North Am. 16: 111-125. 1985.

(Continued)

Primary Examiner—Thomas C Barrett
Assistant Examiner—Sameh Boles
(74) Attorney, Agent, or Firm—Caesar, Rivise, Bernstein, Cohen & Pokotilow, Ltd.

(57) ABSTRACT

A device and method to provide a surgically inserted internal tether between the femur and tibia is provided which will prevent distraction of the healing anterior cruciate ligament in all degrees of flexion and extension, at all times. The anterior cruciate ligament tether preserves the four-bar cruciate linkage, critical for normal knee mechanics. In addition, placement of the tether provides bleeding into the knee in the region of the anterior cruciate ligament attachment sites and the consequent inflow of pluripotential cells and healing mediators.

10 Claims, 6 Drawing Sheets

OTHER PUBLICATIONS

Hseih T, et al. The effects of removal and reconstruction of the anterior cruciate ligament on patellofemoral kinematics. Am J Sports Med. 26: 201-209. 1998.

Ramsey DK, et al. Assessment of functional knee bracing: an in vivo 3-D kinematic analysis of the anterior cruciate deficient knee. Clin Biomech. 16: 61-70. 2001.

Beynnon, BD, et al. The effect of ACL deficiency and functional bracing on translation of the tibia relative to the femur. Am J Sports Med. 31: 99-105. 2003.

Fitzpatrick DC, et al. Knee stability after articulated external fixation. Am J Sports Med. 33: 1735-1741. 2005.

Goodfellow J, O'Connor J. The mechanics of the knee and prosthesis design. J Bone Joint Surg. 60-B: 358-369. 1978.

Velazquez RJ, et al. Complications of use of the Ilizarov technique in the correction of limb deformities in children. J Bone Joint Surg. 75-A: 1148-1156. 1993.

Marshall et al., Primary surgical treatment of anterior cruciate ligament lesions, Am J Sports Med 1982;10:103-7, United States.

Casteleyn, P.P., Management of Anterior Cruciate Ligament Lesions: Surgical Fashion, Personal Whim or Scientific Evidence? Study of Medium- and Long-Term Results, Acta Orthopaedica Beligica, vol. 64-3-1998.

Warren, R.F., Primary repair of the anterior cruciate ligament. Clin Orthop Rel Res. 1983;172:65-70.

O'Donoghue, D. et al., Repair and Reconstruction of the anterior cruciate ligament in dogs. J Bone Joint Surg Am. 1971;53:710-8.

Cabaud, H.E. et al., Experimental studies of acute anterior cruciate ligament injury and repair, Am J Sports Med. 1979;7:18-22.

Eriksson E., Sports injuries of the knee ligaments: their ddiagnosis, treatment, rehabilitation, and prevention, Med Sci Sports, 1976;8:133-44.

Fleming, B.C. et al., Can suture repair of ACL transection restore normal anteroposterior laxity of the knee? An ex vivo study, J Orthop Res., 2008;26:1500-5.

\* cited by examiner

ANTERIOR CRUCIATE LIGAMENT TETHER

CROSS-REFERENCE TO RELATED APPLICATIONS

Not applicable

FEDERALLY SPONSORED RESEARCH

Not applicable

BACKGROUND

1. Field of Invention

This invention relates to anterior cruciate ligament injury and repair.

2. Description of Prior Art

The anterior cruciate ligament (ACL) of the knee functions primarily to resist anterior translation of the tibia with respect to the femur. The ACL also contributes to rotational stability and resists hyperextension. In addition, the ACL has mechanoreceptors which provide proprioception—the conscious awareness of the limb position in space. The ACL may rupture from a variety of contact or noncontact injury mechanisms, especially when severe twisting occurs. The annual incidence of anterior cruciate ligament injuries in the United States is in excess of 100,000.

The ruptured ACL does not typically heal itself. Kurosaka, M., et al. (1998) *J Bone Joint Surg* 80, 1200-1203, reported spontaneous healing of ACL rupture in only two of fifty patients studied. Therefore, the current treatment for this injury is broadly divided into two approaches: activity modification and surgical reconstruction.

Activity modification requires that the patient accommodate to the injury by avoiding those maneuvers that would cause subluxation given absent ACL function. This is not a particularly rewarding strategy. To begin, activity modification demands giving up sports—often the very same activity that the patient was doing at the time of injury, and ostensibly enjoys. Furthermore, the natural history of the ACL-deficient knee is associated with meniscal tears, chondral damage, and degenerative changes. Irvine, G. B. and Glasgow, M. M. S. (1992) *J Bone Joint Surg [Br]* 74, 403-405 reported the incidence of major meniscal tears increases with time from the original ACL injury if untreated. They suggest the menisci undergo gradual attrition from abnormal loading and, in particular, increased shear. Indelicato, P. A. (1983) *J Bone Joint Surg* 65, 323-329 documented that chondral changes in ACL patients are more than twice as frequent in chronic patients who come to arthroscopy than in acute patients, implying that some of this damage was acquired after the injury.

Reconstruction of the ACL—i.e., replacement with a biological graft—as described in U.S. Pat. No. 5,139,520 Rosenberg is the current preferred surgical treatment for ACL rupture. This too is an imperfect solution; the problems encountered with reconstruction include graft site morbidity, inadequate graft to bone healing, and the loss of the proprioceptive function of the ACL. Kocher, M. S., et al. (2006) *J Bone Joint Surg* 84A, 1560-72, reported that on a discrete ordinal scale ranging from 1 to 10, which was framed by a score of 10 indicating "very satisfied", a score between 5 and 6 indicating "neutral", and a score of 1 indicating "very unsatisfied," 15% of patients after ACL reconstruction (31 of 201 patients) had a patient satisfaction score of 5 or lower. Further, ACL reconstruction requires drilling about 10 mm tunnels in order for graft passage. These tunnels may alter the bony architecture which supports the joint surfaces and may cause premature closure of open growth plates in children.

Conspicuously missing from this short list of current treatment options is repair of the torn ligament. Surgeons shun ACL repair not because repair is impossible; suturing torn edges of tissue is a classic procedure and the existence of a Current Procedural Terminology (CPT) code for this operation, 27407, certainly testifies to the fact that people have tried. The reason that surgeons do not regularly perform this operation is simply that it does not work. The first primary repair of the ACL is attributed to A. W. Mayo Robson in 1895. Marshall, J. L., et al. (1979) *Clin Orthop* 143, 97-106 described a popular technique involving figure of 8 suture placement. While short-term results of repair were encouraging, Gollehon, D. L., et al. (1985) *Orthop Clin North Am* 16, 111-124, noted deterioration of these results over time.

The first problem with primary suture repair is technical. The ligament itself is short—measuring only about 33 mm—and is composed of longitudinal fibers. These features, in turn, make it difficult to place a stitch within the ligament and to retain such a stitch if placed, respectively. Ordinarily, when ligaments and tendons are repaired, the stitch is woven through a length of tissue, to have the suture circumferentially grasp the longitudinal fibers. With only 33 mm of tissue to work with, such an approach is not feasible.

Beyond the technical issues, the ACL is thought to have inherently poor healing potential, owing either to inadequate delivery and retention of healing factors from the circulation or to limited retention of these healing factors in the local milieu due to clot dissolution. It is our hypothesis—which serves as the basis of the invention herein described—that ACL repair fails because current methodology does not reestablish the correct and necessary biomechanical environment for healing, and that even if one were to surmount the difficulties in placing a secure stitch as well as delivering and retaining the healing factors, the repair is doomed to failure unless and until that correct and necessary biomechanical environment for healing is created and maintained. This proper environment comprises the maintenance of the native tibia-to-femur distance, full range of motion, and exposure of the ligament to some, but not excessive, mechanical loading.

The ACL is a critical component of the 4-bar cruciate mechanical linkage which dictates the spatial relationship between the femur and the tibia during flexion and extension of the knee. When the ACL is absent, tibiofemoral kinematics become grossly abnormal. Hsieh, Y., et al. (1998) *Am J Sports Med* 26, 201-209, demonstrated that excision of the ACL resulted in an increase in anterior laxity of the knee by a minimum of 5.5 mm at 0 degrees of flexion and a maximum of approximately 15 mm between 45 and 75 degrees of knee flexion. This distraction of the healing ACL results in failure to heal. Even if healing were to take place in the setting of distraction, the healed ligament would be longer than normal and functionally worthless. This underscores the point that the proper tibia-to-femur distance must be maintained.

Placing the knee in a cast can approximately maintain the correct tibia-to-femur distance and prevent distraction of the healing ACL, but the absence of knee motion deprives the healing graft of the mechanical signals it needs for proper maturation (so-called "ligamentization"—i.e., biological transformation into tissue resembling the native ligament). Moreover, immobilization leads to arthrofibrosis (stiffness of the joint) all too frequently. The stiff knee is certainly stable, but the resultant insult to normal range of motion leads to functional impairment in excess of what ligament deficiency itself would impose. Hence, this treatment is worse than the disease it attempts to heal. Further, soft tissue and padding interposed between the cast and the target bones limits precise maintenance of the appropriate distance.

We also note that stabilizing the knee with an extra-articular, indeed extra-corporeal, device, even if hinged, will not allow for maintenance of the precise tibia-to-femur distance. Bracing the knee has been employed as a method for approximating the femur and tibia in the setting of a torn ACL, but this approximation is inadequate to the task. For example, the four-point anterior cruciate ligament brace is described in U.S. Pat. No. 4,697,583 Mason, assigned to DonJoy Orthopedic, Inc. However, functional knee braces fail to completely reduce pathological translations and rotations due to the soft tissue interposed between the braces and the target bones. Ramsey D. K., et al. (2001) *Clinical Biomechanics* 16, 61-70 studied the skeletal kinematics of ACL deficient knees with and without the DonJoy Legend knee brace (Smith and Nephew DonJoy, Carlsbad, USA) and concluded that no consistent reductions in anterior tibial translations were observed as a function of the knee brace tested. Beynnon, B. D., et al. (2003) *Am J Sports Med* 31, 99-105, specifically found that bracing a knee with an ACL tear was not effective in reducing the abnormal anterior translations produced by the change between nonweightbearing and weightbearing postures.

A hinged external fixator capable of holding bony parts by means of screws or pins embedded in the bones was described in U.S. Pat. No. 4,696,293 Ciullo. This hinged external fixator can be used temporarily to rigidly control the relationship of the tibia with respect to the femur while allowing joint motion. However, Fitzpatrick, D. C., et al. (2005) *Am J Sports Med* 33, 1735-1741, reported that following the application of a hinged external fixator to a cruciate-deficient knee, anterior tibial translation with the knee at 30 degrees of flexion was 8.1 mm, compared to 4.5 mm in an intact knee. This pathologic anterior tibial translation is likely present because the true axis of rotation of the knee is not a fixed point—as a hinged device would impose—but rather one that migrates through the range of motion as described by Goodfellow, J. and O'Connor, J. (1978) *J Bone Joint Surg* 60B, 358-369. In addition, external fixators are all-too-frequently complicated by pin tract irritation, pin tract infection, osteomyelitis, fractured pins, and bony insertional pain. Velazquez, R. J., et al. (1993) *J Bone Joint Surg* 75A, 1148-1156, reported 17 pin tract infections for 61 uses of external fixators. Further, the pin tracts may interfere with tunnel placement if an ACL reconstruction is required in the future.

In sum, ACL repairs have failed because, inter alia, the correct biomechanical environment for healing—namely, maintaining the proper distance and tension between the femoral and tibial ACL attachment sites, throughout the full range of motion of the knee, at all times—has not been recreated by any of the methods disclosed in the prior art. The paradox of ACL repair is that the functions of an intact ACL are necessary to allow the repaired ligament to heal normally, yet if these functions were present, repair would not be needed. The instant invention provides a temporary, functional substitute for the injured ligament, allowing the repair to mature in the correct environment.

SUMMARY

The primary object of the instant invention is to provide a surgically inserted internal tether between the femur and tibia in order to establish temporarily the proper mechanical environment comprising: 1) maintenance of the appropriate distance between the femoral and tibial ACL attachment sites; 2) allowance of full range of motion; and 3) permitting exposure of the healing ligament to some, but not excessive, mechanical loading. It is suggested that the instant invention will resist the forces of subluxation such that a repaired ligament can heal in a functionally worthy state.

OBJECTS AND ADVANTAGES

Accordingly, several objects and advantages of the present invention are:

(a) to provide an internal tether temporarily preventing distraction of the healing anterior cruciate ligament in all degrees of flexion and extension, at all times (b) to provide temporary preservation of the four-bar cruciate linkage, critical for normal knee mechanics (c) to provide a surgically created hemarthrosis (bleeding into the knee) in the region of the anterior cruciate ligament attachment sites, facilitating the consequent inflow of pluripotential cells and healing mediators (d) to provide temporary tibiofemoral immobilization at correct isometric, native length (e) to facilitate normal range of motion during immobilization (f) to provide a minimally-invasive procedure to establish temporary stability leading to ligament healing and an optimally functional, stable knee.

Further objects and advantages of the invention will become apparent from a consideration of the drawings and ensuing description.

REFERENCE NUMERALS IN DRAWINGS 10 knee joint
12 femur
14 tibia
15 tibial tubercle
16 lateral condyle
18 lateral meniscus
20 medial condyle
22 medial meniscus
24 intercondylar notch
26 femoral shaft
28 anterior cruciate ligament (ACL)
30 ACL femoral attachment site
32 ACL tibial attachment site
34 posterior cruciate ligament (PCL)
36 PCL femoral attachment site
38 PCL tibial attachment site
40 four-bar linkage
42 femoral link
44 tibial link
46 femoral tunnel
48 tibial tunnel
50 tether
52 femoral bone bridge
54 tibial bone bridge
56 drill
58 tip
60 shaft
62 eyelet
64 femoral standard button
66 tibial standard button
68 femoral suture anchor
69 tibial suture anchor
70 tibial guide
72 drill path

DESCRIPTION—MAIN EMBODIMENT

The present invention provides an internal tether in all degrees of flexion and extension, preventing temporary distraction of the healing anterior cruciate ligament (ACL). Although specific embodiments of the invention have been selected for illustration in the drawings and although specific terms will be used in the description which follows, such selection and terms are not intended to limit the scope of the invention, which is defined in the appended claims.

Figure 1A:
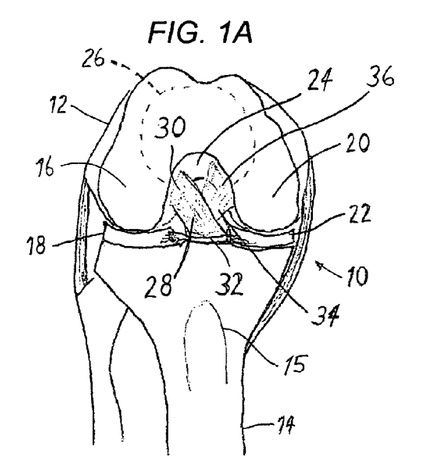
FIG. 1A is a front elevational view of a flexed right human knee joint having the skin and muscle tissue removed along with the patella, for ease of view of the intact anterior cruciate ligament.

FIG. 1A is a front elevational view of a flexed right human knee joint 10 having the skin and muscle tissue removed along with the patella. Knee joint 10 is formed by the lowermost portion of femur 12 and the uppermost portion of tibia 14. Lateral condyle 16 of femur 12 is in contact with tibia 14 and lateral meniscus 18. Medial condyle 20 of femur 12 is in contact with tibia 14 and medial meniscus 22. Intercondylar notch 24 separates condyles 16 and 20. Femoral shaft 26 is the upper continuation of condyles 16 and 20 and is depicted by hidden lines since knee joint 10 is flexed ninety degrees. Tibial tubercle 15 is a bony prominence and landmark on the anterior aspect of tibia 14. Tibia 14 and femur 12 pivot at their contact points. One of the ligaments that connects tibia 14 and femur 12 together is anterior cruciate ligament 28, which is connected to tibia 14 at ACL tibial attachment site 32 and passes upwardly, rearwardly, and laterally and connects with femur 12 at ACL femoral attachment site 30 of lateral condyle 16, near rear of intercondylar notch 24. Another ligament that connects tibia 14 and femur 12 together is the posterior cruciate ligament 34, which is connected to femur 12 at PCL femoral attachment site 36 of medial condyle 20 and passes downwardly, rearwardly, and laterally behind anterior cruciate ligament 28 to connect with rear aspect of tibia 14.

Figure 1B:
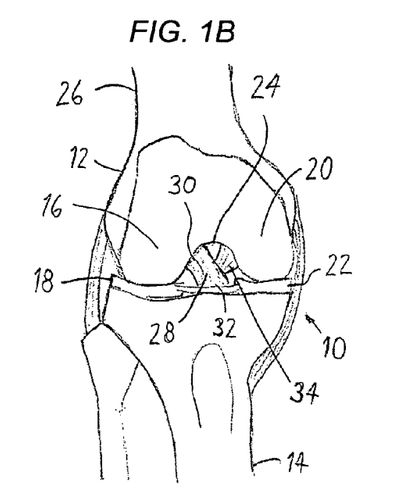
FIG. 1B is a front elevational view of an extended right human knee joint having the skin and muscle tissue removed along with the patella, for ease of view of the intact anterior cruciate ligament.

FIG. 1B is a front elevational view of an extended right human knee joint 10 having the skin and muscle tissue removed along with the patella. Again, lateral condyle 16 of femur 12 is in contact with tibia 14 and lateral meniscus 18. Medial condyle 20 of femur 12 is in contact with tibia 14 and medial meniscus 22. Intercondylar notch 24 separates condyles 16 and 20. Femoral shaft 26 is the upper continuation of condyles 16 and 20. Anterior cruciate ligament 28 is connected to tibia 14 at tibial attachment site 32 and passes upwardly, rearwardly, and laterally and connects with femur 12 at the femoral attachment site 30 of lateral condyle 16, near rear of intercondylar notch 24. Posterior cruciate ligament 34 also connects tibia 14 to femur 12.

Figure 1C:
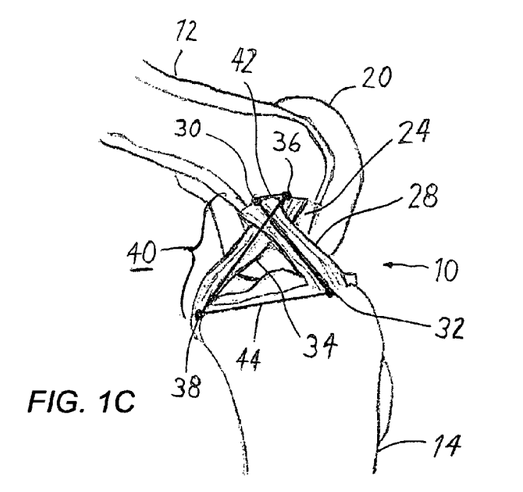
FIG. 1C is a side view of a portion of a typical right knee joint, in the plane of the anterior cruciate ligament, partly in section with part of the lateral condyle of the femur removed along with all the external ligaments and the patella for ease of view of all components of the four-bar linkage.

FIG. 1C is a side view of a portion of a typical right knee joint 10, in the plane of anterior cruciate ligament 28, partly in section with part of lateral condyle of femur 12 removed along with all the external ligaments and the patella for ease of view of all components of four-bar linkage 40. Knee joint 10, formed by femur 12 and tibia 14, is flexed sixty degrees. Anterior cruciate ligament 28 is connected to tibia 14 at tibial attachment site 32 and passes upwardly, rearwardly, and laterally and connects with femur 12 at the femoral attachment site 30, near rear of intercondylar notch 24. Posterior cruciate ligament 34 is connected to femur 12 at PCL femoral attachment site 36 of medial condyle 20 and passes downwardly, rearwardly, and laterally behind anterior cruciate ligament 28 to connect with tibia 14 at PCL tibial attachment site 38. Femoral link 42 is composed of the portion of femur 12 connecting ACL femoral attachment site 30 and PCL femoral attachment site 36. Tibial link 44 is composed of the portion of tibia 14 connecting ACL tibial attachment site 32 and PCL tibial attachment site 38. Four-bar linkage 40 consists of femoral link 42, tibial link 44, anterior cruciate ligament 28, and posterior cruciate ligament 34. Four-bar linkage 40 dictates the spatial relationship between the femur 12 and the tibia 14 during flexion and extension of knee joint 10.

Figure 2A:
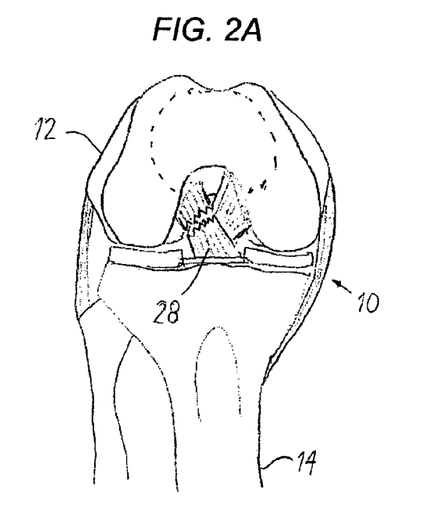
FIG. 2A is a front elevational view of a flexed right human knee joint having the skin and muscle tissue removed along with the patella, for ease of view of the ruptured anterior cruciate ligament.
Figure 2B:
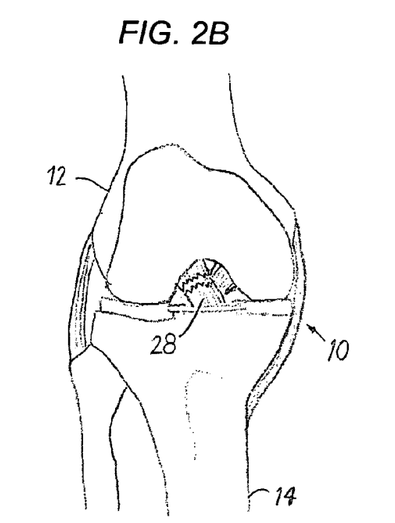
FIG. 2B is a front elevational view of an extended right human knee joint having the skin and muscle tissue removed along with the patella, for ease of view of the ruptured anterior cruciate ligament.
Figure 2C:
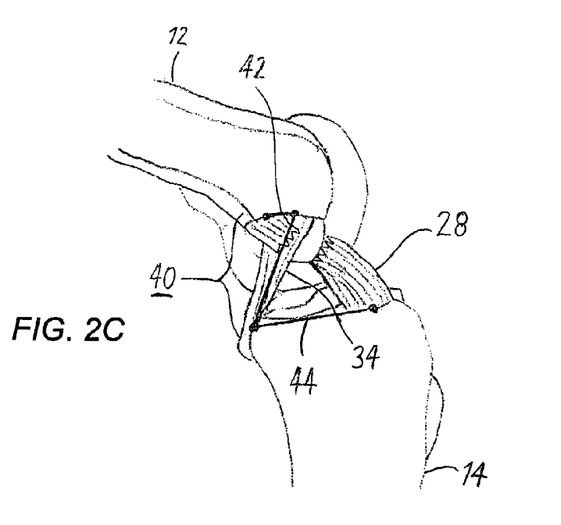
FIG. 2C is a side view of a portion of a right knee joint, in the plane of the anterior cruciate ligament, partly in section with part of the lateral condyle of the femur removed along with all the external ligaments and the patella for ease of view of all components of the four-bar linkage, with rupture of the anterior cruciate ligament link and consequent anterior subluxation of the tibia.

FIGS. 2A, 2B, and 2C are identical views of right knee joint 10 to FIGS. 1A, 1B, and 1C, respectively, except that anterior cruciate ligament 28, which connects femur 12 to tibia 14, is ruptured. FIG. 2C further depicts that four-bar linkage 40 is incomplete, consisting of only femoral link 42, tibial link 44, and posterior cruciate ligament 34. Consequently, tibia 14 is translated forward with respect to femur 12 since anterior cruciate ligament 28 is not competent. This pathologic forward translation of tibia 14 is also called anterior subluxation.

Figure 3A:
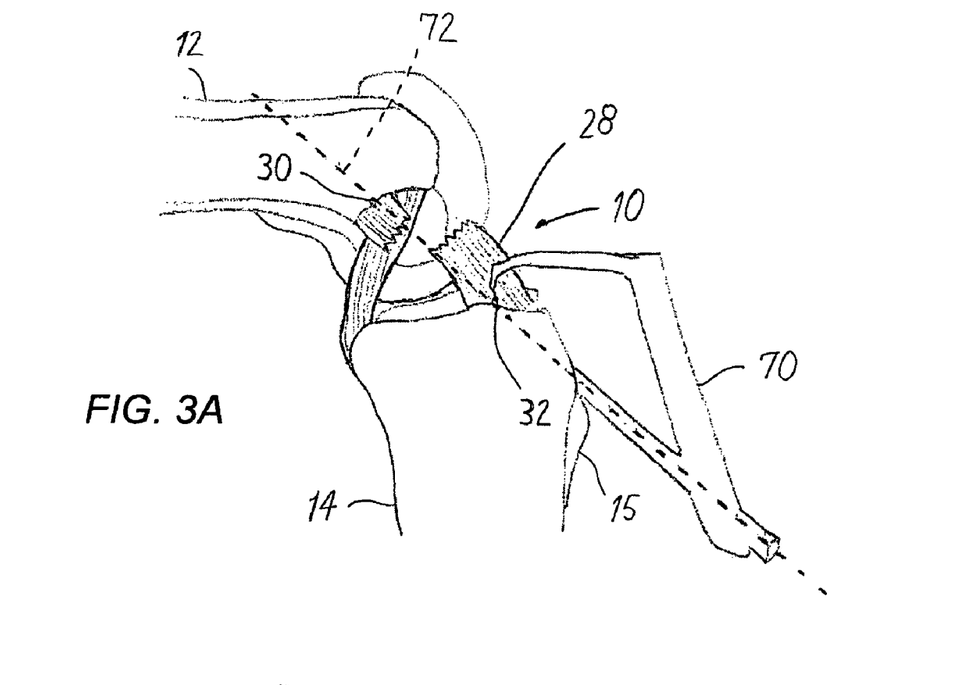
FIG. 3A is a side view of a portion of a right knee joint, in the plane of the anterior cruciate ligament, partly in section with part of the lateral condyle of the femur removed along with all the external ligaments and the patella for ease of view of proper placement of the tibial drill locating and orientation device.

FIGS. 3A, 3B, 3C, and 3D depict a technique potentially used in placement of ACL tether. The patient is placed in a supine position and anesthesia is administered. Arthroscopic portals are established (though the instant invention is easily used with open surgery if desired). FIG. 3A is a side view of a portion of right knee joint 10, in the plane of anterior cruciate ligament 28, partly in section with part of lateral condyle of femur 12 removed along with all the external ligaments and the patella. Knee joint 10 is flexed ninety degrees. Tibial guide 70 is utilized to ensure proper location and orientation of drill path 72. Tibial guide 70 may be of the type disclosed in U.S. Pat. No. 4,739,751 Sapega, which serves as a locating and orientating apparatus. Internally the guide is positioned at the ACL tibial attachment site 32. Externally the guide is positioned midway between tibial tubercle 15 and medial aspect of tibia 14. Ideally, drill path 72 will be coincident with both ACL tibial attachment site 32 and ACL femoral attachment site 30 in order to ensure proper isometry.

Figure 3B:
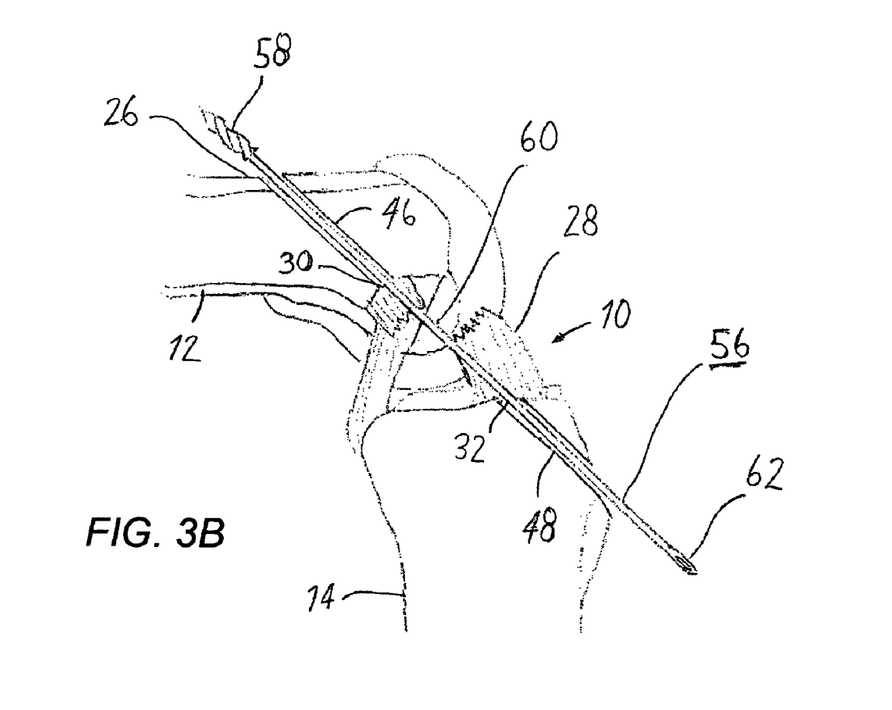
FIG. 3B is a side view of a portion of a right knee joint, in the plane of the anterior cruciate ligament, partly in section with part of the lateral condyle of the femur removed along with all the external ligaments and the patella for ease of view of tibial and femoral tunnels immediately after drilling.

FIG. 3B is a similar side view of a portion of right knee joint 10, in the plane of anterior cruciate ligament 28, illustrating drilling technique. Drill 56 consists of a tip 58, a shaft 60, and an eyelet 62. The diameter of tip 58 is greater than the diameter of shaft 60 in order to permit easy forward sliding of drill 56 after tunnels are established. Drill 56 is placed through the tibial guide and tibial tunnel 48 is drilled into the joint. Under direct arthroscopic visualization drill 56 is advanced toward ACL femoral attachment site 30. The drill is advanced through femur 12 to femoral shaft 26 and exits the skin of the anterolateral thigh. Tibial tunnel 48 passes from anterior surface of tibia 14 to ACL tibial attachment site 32. Femoral tunnel 46 passes from ACL femoral attachment site 30 to anterior surface of femoral shaft 26. The tether may be shuttled through tunnels 48 and 46 by placing a portion of the tether through eyelet 62 and then pulling drill 56 upward and completely through tunnels 48 and 46.

Figure 3C:
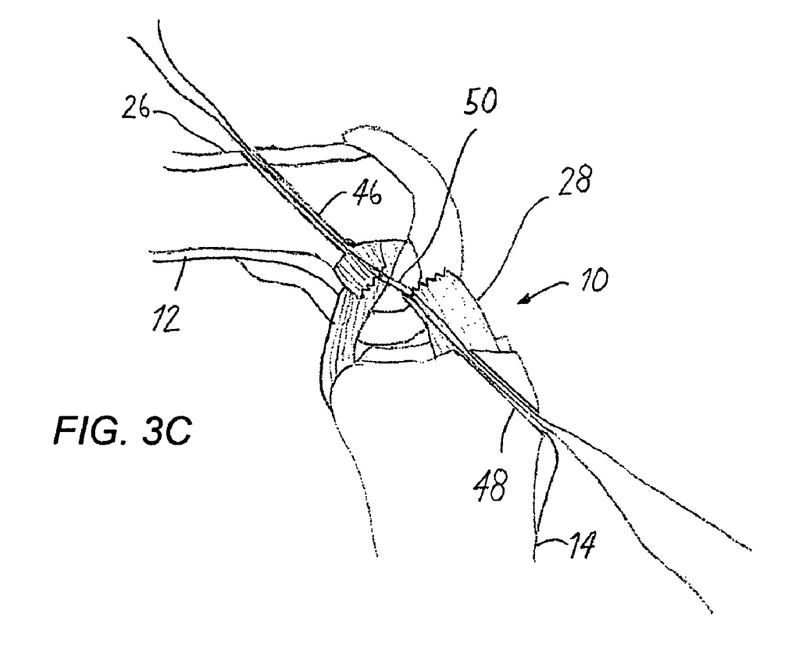
FIG. 3C is a side view of a portion of a right knee joint, in the plane of the anterior cruciate ligament, partly in section with part of the lateral condyle of the femur removed along with all the external ligaments and the patella for ease of view of device placement within the tibial and femoral tunnels.

FIG. 3C is a side view of a portion of a right knee joint 10, in the plane of anterior cruciate ligament 28, depicting knee joint 10 after placement of tether 50 from anterior surface of tibia 14, through tibial tunnel 48, through knee joint 10, through femoral tunnel 46, and out anterior aspect of shaft 26 of femur 12. Tether 50 is a flexible, elongate material of sufficient strength and stiffness, such as two strands of suture in this case.

Figure 3D:
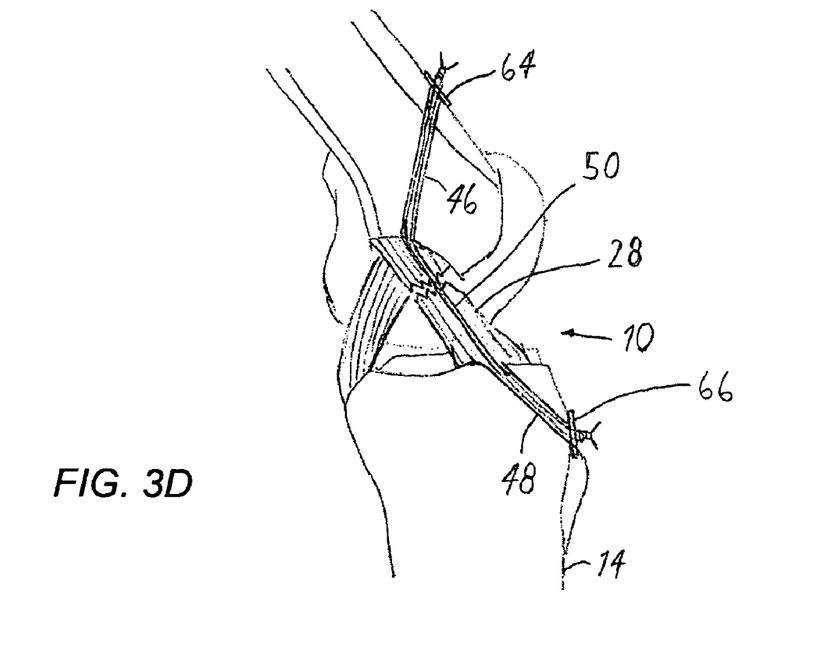
FIG. 3D is a side view of a portion of a right knee joint, in the plane of the anterior cruciate ligament, partly in section with part of the lateral condyle of the femur removed along with all the external ligaments and the patella for ease of view of tibial and femoral fixation.

FIG. 3D is a side view of a portion of right knee joint 10, in the plane of anterior cruciate ligament 28, illustrating knee joint 10 in thirty degrees of flexion. The uppermost free ends of tether 50 are tied over femoral standard button 64. The diameter of button 64 must be greater than the diameter of femoral tunnel 46 to ensure secure femoral fixation without slippage. With the knee joint 10 in thirty degrees of flexion and a rearward-directed force applied to the tibia 14, the lowermost free ends of tether 50 are similarly tied over tibial standard button 66. Again, the diameter of button 66 must be greater than the diameter of tibial tunnel 48 to ensure secure tibial fixation without slippage.

Figure 4A:
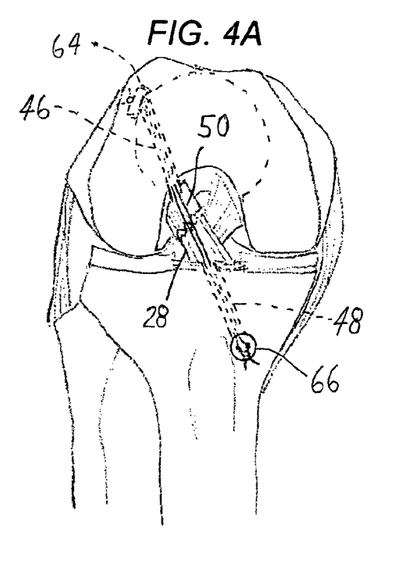
FIG. 4A is a front elevational view of a flexed right human knee joint having the skin and muscle tissue removed along with the patella, after placement of the anterior cruciate ligament tether.
Figure 4B:
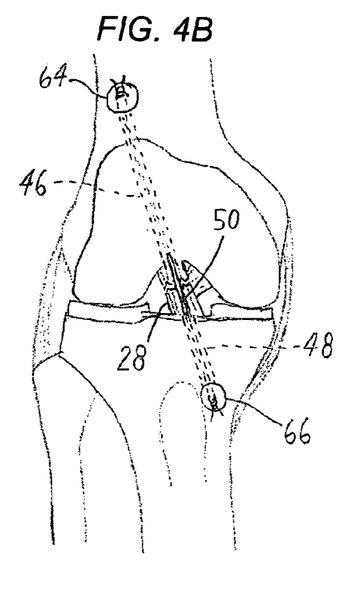
FIG. 4B is a front elevational view of an extended right human knee joint having the skin and muscle tissue removed along with the patella, after placement of the anterior cruciate ligament tether.
Figure 4C:
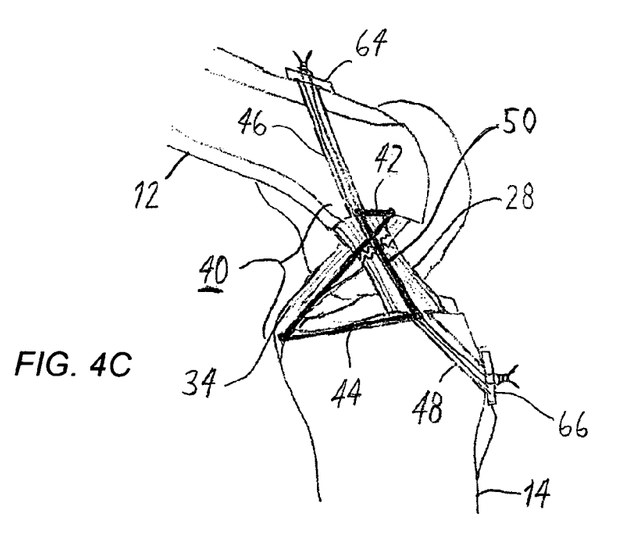
FIG. 4C is a side view of a portion of a typical right knee joint, in the plane of the anterior cruciate ligament, partly in section with part of the lateral condyle of the femur removed along with all the external ligaments and the patella for ease of view of all components of the four-bar linkage, with the anterior cruciate ligament tether acting as the anterior cruciate ligament link.

FIGS. 4A, 4B, and 4C are identical to FIGS. 1A, 1B, and 1C, respectively, except that anterior cruciate ligament 28 is ruptured and tether 50 is placed through femoral tunnel 46 and tibial tunnel 48. Femoral fixation consists of the uppermost free ends of tether 50 tied over femoral standard button 64. Tibial fixation consists of the lowermost free ends of tether 50 tied over tibial standard button 66. FIG. 4C further depicts that four-bar linkage 40 is again complete, consisting of femoral link 42, tibial link 44, posterior cruciate ligament 34, and tether 50. Consequently, tibia 14 is not translated forward with respect to femur 12 despite that anterior cruciate ligament 28 is not competent.

OPERATION—MAIN EMBODIMENT

The anterior cruciate ligament tether 50 is secured to femur 12 and to tibia 14 (see FIGS. 4A, 4B, and 4C). Tether 50 passes through ACL tibial attachment site 32 as well as ACL femoral attachment site 30. Consequently, tether 50 limits the maximum distance between ACL tibial attachment site 32 and ACL femoral attachment site 30. Further, four-bar linkage 40 is restored by tether 50, allowing maintenance of this fixed distance between attachment sites 30 and 32 throughout the entire range of knee joint 10 motion.

In this manner, tether 50 prevents distraction of the healing anterior cruciate ligament 28 in all degrees of flexion and extension, at all times. In addition, placement of tether 50 requires drilling into the bone near ACL attachment sites 30 and 32. This drilling provides bleeding into the knee and the consequent inflow of pluripotential cells and healing mediators.

DESCRIPTION AND
OPERATION—ALTERNATIVE EMBODIMENTS

Figure 5:
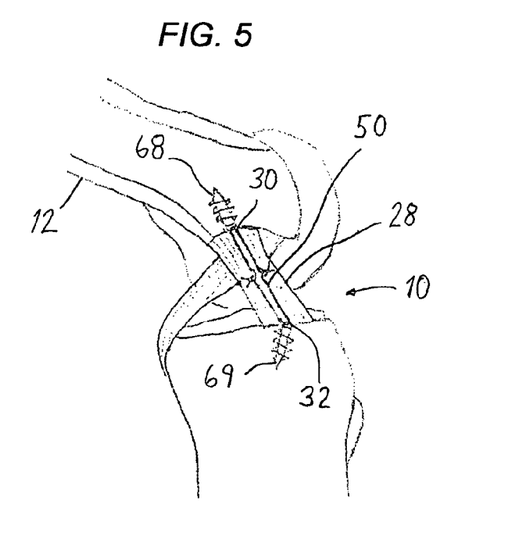
FIG. 5 is a side view of a portion of a typical right knee joint, in the plane of the anterior cruciate ligament, partly in section with part of the lateral condyle of the femur removed along with all the external ligaments and the patella for ease of view of an alternate embodiment utilizing suture anchors.

FIG. 5 is a side view of a portion of right knee joint 10, in the plane of anterior cruciate ligament 28, partly in section with part of lateral condyle of femur 12 removed along with all the external ligaments and the patella. An alternative embodiment of the anterior cruciate ligament tether involves employing any type of suture anchor as part of femoral fixation or tibial fixation. For example, anchor may be of the type disclosed in U.S. Pat. No. 5,370,662, which has a self-drilling, tapping leading end and a trailing end of suture. Through an arthroscopic portal, femoral suture anchor 68 is inserted directly into ACL femoral attachment site 30. Similarly, through another arthroscopic portal, tibial suture anchor 69 is inserted directly into the ACL tibial attachment site 32. With knee joint 10 in thirty degrees of flexion and a rearward-directed force applied to the tibia 14, the suture from femoral anchor 68 is secured to the suture from tibial anchor 69 using standard arthroscopic knot-tying techniques, forming tether 50.

Figure 6:
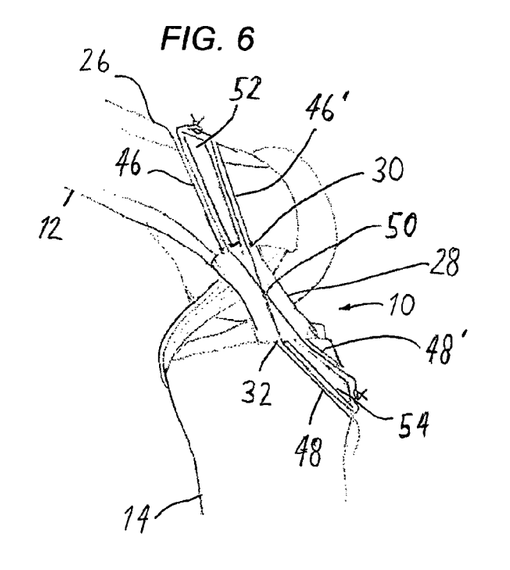
FIG. 6 is a side view of a portion of a typical right knee joint, in the plane of the anterior cruciate ligament, partly in section with part of the lateral condyle of the femur removed along with all the external ligaments and the patella for ease of view of an alternate embodiment featuring multiple tunnels.

FIG. 6 is a side view of a portion of right knee joint 10, in the plane of anterior cruciate ligament 28, partly in section with part of lateral condyle of femur 12 removed along with all the external ligaments and the patella, in order to demonstrate alternate embodiment of multiple tunnel technique in femur 12 and tibia 14. Femoral tunnels 46 and 46' start in ACL femoral attachment site 30 and exit different points on cortex of femoral shaft 26. Tibial tunnels 48 and 48' start in ACL tibial attachment site 32 and exit different points on anterior cortex of tibia 14. A flexible, elongate material of sufficient strength and stiffness will be passed through each tunnel. Tether 50 is comprised of all of these materials. The uppermost free ends of tether 50 are tied over the femoral bone bridge 52 which separates femoral tunnels 46 and 46'. Next, with the knee joint 10 in thirty degrees of flexion and a rearward-directed force applied to the tibia 14, the lowermost free ends of tether 50 are similarly tied over the tibial bone bridge 54 which separates tibial tunnels 48 and 48'.

Operation of the alternative embodiments is identical to operation of the preferred embodiment. Specifically, tether 50 limits the maximum distance between ACL attachment sites 30 and 32 and, consequently, prevents distraction of the healing anterior cruciate ligament 28 in all degrees of flexion and extension, at all times. In addition, placement of tether 50 requires violating the bone near ACL attachment sites 30 and 32. This activity provides bleeding into the knee and the consequent inflow of pluripotential cells and healing mediators.

CONCLUSION, RAMIFICATIONS, AND SCOPE

Thus, the reader will see that the Anterior Cruciate Ligament Tether provides the proper biomechanical environment for healing of a ruptured anterior cruciate ligament. The tether restores the 4-bar cruciate mechanical linkage and prevents distraction of the healing anterior cruciate ligament in all degrees of flexion and extension, at all times. Usage of the Tether may permit anterior cruciate ligament primary healing and repair, thereby avoiding the problems associated with the natural history of an anterior cruciate-deficient knee as well as the complications associated with anterior cruciate ligament reconstruction.

While the above description contains many specificities, these should not be construed as limitations on the scope of the invention, but rather as an exemplification of one preferred embodiment thereof. Many other variations are possible. For example, proper placement of the tether may be aided by arthroscopic visualization, radiographic evaluation, or computer-aided guidance utilizing three-dimensional arrays as well as by tibial and femoral locating and orientation guides.

Accordingly, the scope of the invention should be determined not by the embodiments illustrated, but by the appended claims and their legal equivalents.

We claim:

1. A method for temporarily holding a tibia and a femur of a knee together in setting a ruptured anterior cruciate ligament, comprising steps of: (a) inserting a flexible, elongate material having a tibial portion and a femoral portion into the knee; (b) securing said femoral portion of said material to said femur at anatomic attachment of the anterior cruciate ligament; and (c) securing said tibial portion of said material to said tibia at the anatomic attachment of the anterior cruciate ligament, whereby said material mimics native anterior cruciate ligament function by maintaining physiological distance between said femur and said tibia during motion thus preventing distraction of the healing anterior cruciate ligament in all degrees of flexion and extension during healing of the ruptured anterior cruciate ligament.

2. The method of claim 1, wherein the material is a tether or a surgical suture.

3. The method of claim 1, wherein the material is biocompatible and bioresorbable.

4. The method of claim 1, wherein the step for securing the material to the femur comprises: (a) establishing a bony tunnel which starts at the anatomic femoral attachment of the anterior cruciate ligament and finishes at femoral cortex; (b) passing the material through the bony tunnel; and (c) securing the material to the femur using a device selected from a group consisting of elongated buttons, staples, screws, and regular buttons.

5. The method of claim 1, wherein the step for securing the material to the tibia comprises: (a) establishing a bony tunnel which starts at the anatomic tibial attachment of the anterior cruciate ligament and finishes at tibial cortex; (b) passing the material through the bony tunnel: and (c) securing the material to the tibia using a device selected from a group consisting of elongated buttons, staples, screws, and regular buttons.

6. The method of claim 1, wherein at least one of the securing steps comprises:
(a) placing a suture anchor at the anatomic attachment of the anterior cruciate ligament; and
(b) attaching the material to the suture anchor.

7. The method of claim 1, wherein the step for securing the femoral portion of material comprises: (a) establishing multiple bony tunnels which start at the femoral attachment of the anterior cruciate ligament and finish at different points on femoral cortex; (b) partial passing of a piece of the material through each bony tunnel; and (c) tying the material together over cortical bony bridges between the tunnels.

8. The method of claim 1, wherein the step for securing the tibial portion of material comprises: (a) establishing of multiple bony tunnels which start at the tibial attachment of the anterior cruciate ligament and finish at different points on tibial cortex; (b) partial passing of a piece of the material through each bony tunnel; and (c) tying the material together over cortical bony bridges between the tunnels.

9. The method of claim 1, wherein at least one of the securing steps comprises chemical bonding.

10. The method of claim 1, wherein at least one of the securing steps comprises interference fixation.

* * * * *